(12) United States Patent
Lampropoulos et al.

(10) Patent No.: US 6,402,723 B1
(45) Date of Patent: Jun. 11, 2002

(54) INLINE HEMOSTASIS VALVE

(75) Inventors: Fred P. Lampropoulos, Sandy; Brian W. Stevens, Pleasant Grove, both of UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 09/293,609

(22) Filed: Apr. 16, 1999

(51) Int. Cl.[7] .............................................. A61M 5/14
(52) U.S. Cl. ..................................................... 604/256
(58) Field of Search ........................... 604/167.1, 167.5, 604/236, 256, 278, 32, 167.03; 600/577, 579

(56) References Cited

U.S. PATENT DOCUMENTS

| | | | |
|---|---|---|---|
| 5,059,186 A | 10/1991 | Yamamoto et al. | 604/280 |
| 5,106,054 A * | 4/1992 | Mollenauer et al. | 604/256 |
| 5,167,636 A | 12/1992 | Clement | 604/167 |
| 5,651,170 A | 7/1997 | Stevens | 29/450 |
| 5,693,025 A | 12/1997 | Stevens | 604/167 |

* cited by examiner

*Primary Examiner*—Jeffrey R. Jastrzab
(74) *Attorney, Agent, or Firm*—Workman, Nydegger, Seeley

(57) ABSTRACT

A hemostasis valve apparatus includes (i) a valve body having a lumen therethrough; (ii) a first resiliently deformable seal disposed within the valve body; and (iii) a plunger having a lumen extending therethrough. A passageway extends through the lumens of the plunger and valve body. A cap movably coupled to the valve body selectively moves the plunger along the valve body, thereby selectively compressing the seal. A connector coupled to the plunger is configured to couple the plunger in fluid communication with a fluid delivery means for delivering fluid to the valve. The valve has a substantially linear configuration for convenient storage and use. The valve also features a second seal for sealing the passageway extending through the lumens.

14 Claims, 6 Drawing Sheets

INLINE HEMOSTASIS VALVE

BACKGROUND OF THE INVENTION

1. The Field of the Invention

The present invention relates to valves, and, in particular, relates to hemostasis valves.

2. Relevant Technology

Various medical procedures require temporary and often repeated introduction and removal of catheters and/or guide wires within the cardiovascular system of a patient. For example, using only a relatively small incision, a catheter can be introduced into a blood vessel of a patient and used to position a balloon, implant a stent or deliver a fluid directly to a predetermined location within the cardiovascular system. Catheters can also be used for exploratory surgery and for removing tissue samples within a patient's body, for example.

Operations using catheters can often require the insertion and removal of several different types of catheters and guide wires, which can be employed to guide catheters to a desired location within the body. One problem encountered with the insertion, removal and adjustment of catheters and guide wires is controlling bleeding at the point where the catheters and guide wires are first introduced into the cardiovascular system. In one approach to controlling bleeding and ensuring easy insertion and removal of the catheter and/or guide wire within the cardiovascular system, one end of a hollow introducer is first secured within a large blood vessel of a patient. The opposite end of the introducer is positioned outside the body of the patient and is attached to an adapter.

Such an adapter typically comprises a short, rigid tube having a passageway extending therethrough. Attached at one end of the adapter tube is a connector. The connector is used to connect the passageway of the adapter tube to the exposed end of the introducer. This enables fluids and/or medical instruments, such as catheters and guide wires, to pass between the adaptor tube and the introducer.

Positioned at the opposite end of the adaptor tube is a valve commonly referred to as a hemostasis valve. The hemostasis valve typically includes one or more seals positioned within a valve body. During use of the adaptor, the pressure of the blood of the patient caused by the beating of the patient's heart can cause blood from the patient to flow through the introducer and into the passageway of the adaptor tube. The one or more seals prevent blood from escaping out of the adaptor through the access of the valve.

Typical hemostasis valve adaptors feature a "Y" shape or "T" which enables the adaptor to (i) receive an elongate member through an opening in the body of the adaptor; and (ii) receive a fluid delivered through a secondary access tube of the adaptor. The secondary access tube requires space for storage and use in addition to the space required by the longitudinal body of the adaptor.

Furthermore, it is often desirable to selectively, temporarily affix a medical instrument such as a guidewire or a catheter to a valve during a medical procedure. Loose, sliding instruments can be inadvertently moved within or withdrawn from a desired location within a patient's body. A number of different methods are available for selectively affixing medical instruments within an adaptor.

In one effort to selectively affix a wire to a desired location within a valve, a flow switch is employed. The flow switch has (i) an open position in which fluid or a wire can pass through the switch; and (ii) a closed position which does not permit fluid flow or wire movement. The closed position is achieved through the use of a roller clamp. However, upon clamping a wire in a fixed position through the use of the roller clamp, it is possible to permanently bend or crimp the wire. Typical guide wires and other medical grade wires are delicate, thin elongate instruments and are readily subject to such crimping and bending when used in conjunction with such a clamp, which can significantly hamper the practitioner's ability to use the instrument.

There is therefore a need in the art for a space efficient, reliable hemostasis valve which can selectively maintain a wire such as a guidewire in a desired position without crimping the wire and without allowing blood loss through the valve.

SUMMARY AND OBJECTS OF THE INVENTION

It is therefore an object of the present invention to provide an improved hemostasis valve.

It is another object of the present invention to provide a space efficient hemostasis valve.

It is another object of the present invention to provide a hemostasis valve which minimizes the loss of body fluids during insertion, repositioning, or removal of medical instruments, such as catheters and guide wires, from the hemostasis valve.

It is another object of the present invention to provide an improved hemostasis valve that is capable of being opened to allow fluid to pass therethrough without fluid leaking from the hemostasis valve.

It is another object of the present invention to provide a hemostasis valve which is configured for high pressure injections through the valve.

It is another object of the present invention to provide a hemostasis valve which does not leak during high pressure injections through the valve.

It is a further object of the present invention to provide an improved hemostasis valve which can selectively affix a wire such as a guidewire within the valve without permanently bending or crimping the wire.

It is a further object of the present invention to provide an improved hemostasis valve which can selectively serve as a handle, steering device or torquing device for a wire or other elongated medical instrument.

Still another object of the invention is to provide a hemostasis valve having a substantially linear configuration.

Still another object of the present invention is to provide an improved hemostasis valve that enables the insertion, repositioning or removal of a catheter or guide wire with increased speed and substantially without the loss of body fluids.

Still another object of the invention is to provide an improved valve system for selectively coupling to an elongate instrument such as a wire and/or a fluid delivery means.

To achieve the foregoing objects, in accordance with the invention as embodied and broadly described herein, a hemostasis valve apparatus is provided that is adapted for accessing the cardiovascular system of a patient. A hemostasis valve apparatus of the present invention comprises: (i) a valve body; (ii) a first resiliently deformable seal disposed within the valve body; and (iii) a plunger movably coupled to the valve body so as to selectively open and close the seal.

The valve body and the plunger each have a lumen therethrough. The valve body lumen has a distal valve opening and the plunger lumen has a proximal valve opening. The plunger is movably coupled to the valve body such that a passageway extends from the distal valve opening to the proximal valve opening through the lumens of the plunger and valve body.

The first seal includes a longitudinal flow path therethrough which communicates with the lumen of the valve body when the first seal is in an open position. The first seal assumes a normally open position when not subjected to a compressive force by the plunger, but responds to a compressive force by the plunger to reduce the size of the flow path. When a compressive force is exerted on the compressible seal, a portion of the compressible seal moves radially inward to form a progressively tighter seal. The amount of compressive force that is being exerted on the compressible seal can be incrementally adjusted so as to selectively and progressively reduce the size of the flow path.

The resiliently deformable seal can couple a delicate medical instrument such as a guidewire, occluding wire, or other wire, in a fixed position within the valve without crimping or otherwise damaging the medical instrument.

The resiliently deformable seal sits within a compression chamber of the valve body. The plunger is configured to selectively exert compressive force on the first seal, either through direct contact or indirect contact. By moving back and forth between first and second positions with respect to the valve body, the plunger selectively opens and closes the first seal.

A second seal seals the passageway extending from the distal valve opening to the proximal valve opening through the lumens of the plunger and valve body. The second seal thus prevents fluid from flowing out of a location intermediate the proximal and distal valve openings. In one embodiment, the second seal comprises a resilient O-ring disposed about the distal end of the plunger, which is inserted within the valve body. The O-ring abuts the interior surface of the valve body, sliding along the interior surface of the valve body as the plunger is moved back and forth within the valve body. Preferably, the O-ring is located within an annular groove within the distal end of the plunger.

A connector, e.g., a Luer connector, is coupled to the proximal end of the plunger for coupling a fluid delivery means for delivering fluid in fluid communication with the passageway of the valve. The proximal connector on the plunger, combined with a resiliently deformable first seal provides a unique, reliable, efficient valve for selectively (i) injecting fluid through the valve; and/or (ii) coupling a delicate, elongate instrument to the valve.

The valve body comprises an elongate tubular body which preferably has a solid tubular body wall extending from a proximal end of the tubular body to a distal end of the tubular body. Since the plunger has a connector for coupling to a fluid delivery means, the valve body does not require the use of a secondary fluid access tube extending from the valve body, as with typical adaptors having hemostasis valves. Consequently, the valve is not required to have a "Y" or "T" configuration, but can feature a substantially linear configuration, i.e. substantially straight, which is convenient for storage and use.

The plunger also comprises a tubular body which preferably has a solid tubular body wall extending from a proximal end of the tubular body to the distal end of the tubular body. The plunger and valve body each further comprise at least one and preferably a plurality of wings extending from each tubular body.

The second seal withstands significant fluid pressure by sealing the passageway defined by the plunger and valve bodies. The second seal seals the passageway even when the first seal is in the open, uncompressed position and the valve is coupled to a fluid delivery means. Thus, the valve apparatus of the present invention is particularly useful for high pressure fluid injections in which a fluid delivery means is coupled to the proximal end of the plunger and fluid is injected through the plunger and an opened, uncompressed first seal. The valve apparatus of the present invention is thus advantageous over typical Touhy Borst type valves in which blood can escape through the threads of the valve when the seal of the valve is in an uncompressed position.

By way of example, the valve of the present invention can be used as (i) an adaptor coupled to an introducer which receives elongate instruments or fluid therethrough; (ii) a handle or steering device which grips a medical instrument and which is grasped by a practitioner as the instrument is oriented into a desired location; (iii) a torquing device designed to rotate an elongate member such as a coiled member affixed within the valve; (iv) a fluid injection adaptor for receiving high pressure injections therethrough; and/or (v) a variety of other uses.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention relates to an improved hemostasis valve that can couple to a medical instrument such as a guidewire without damaging the medical instrument and can withstand high pressure injections therethrough without leaking.

Figure 1:
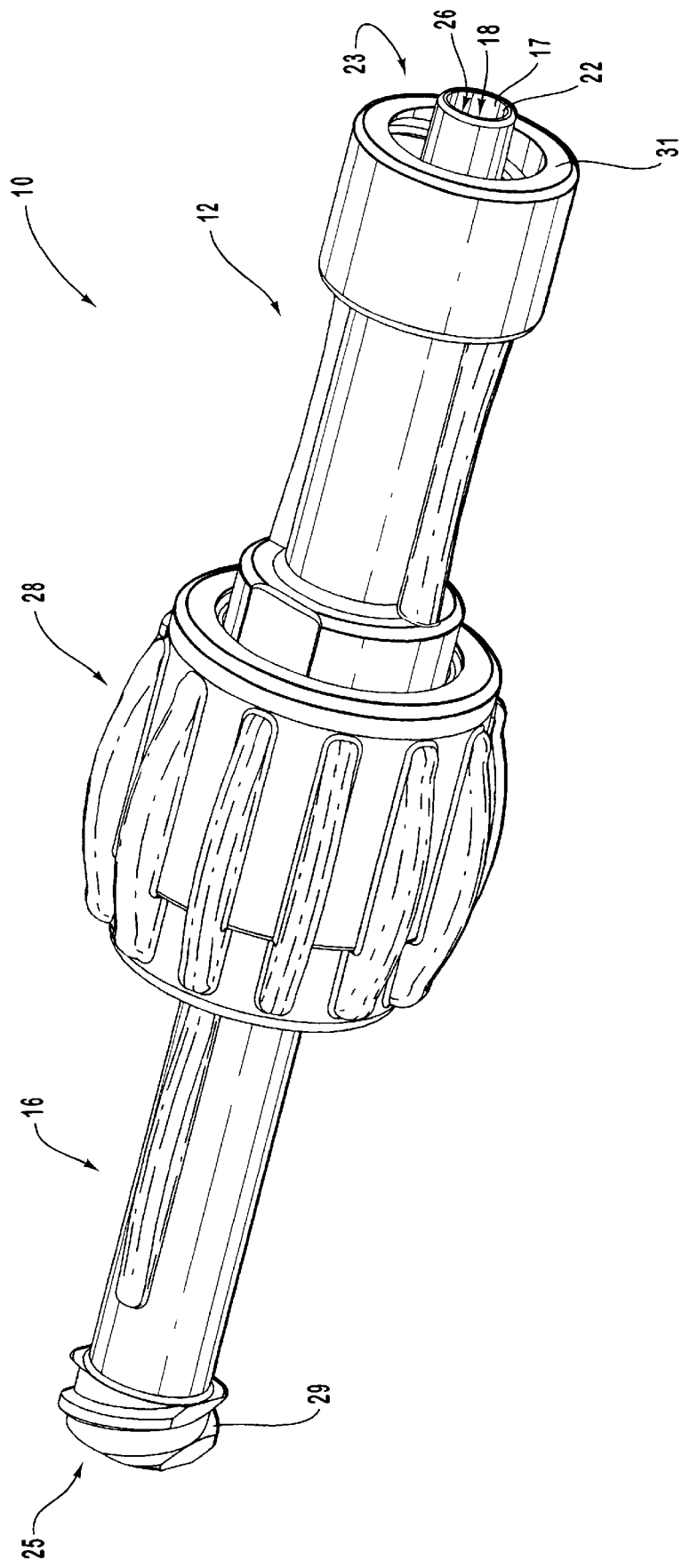
FIG. 1 is a perspective view of a hemostasis valve apparatus of the present invention.
Figure 2:
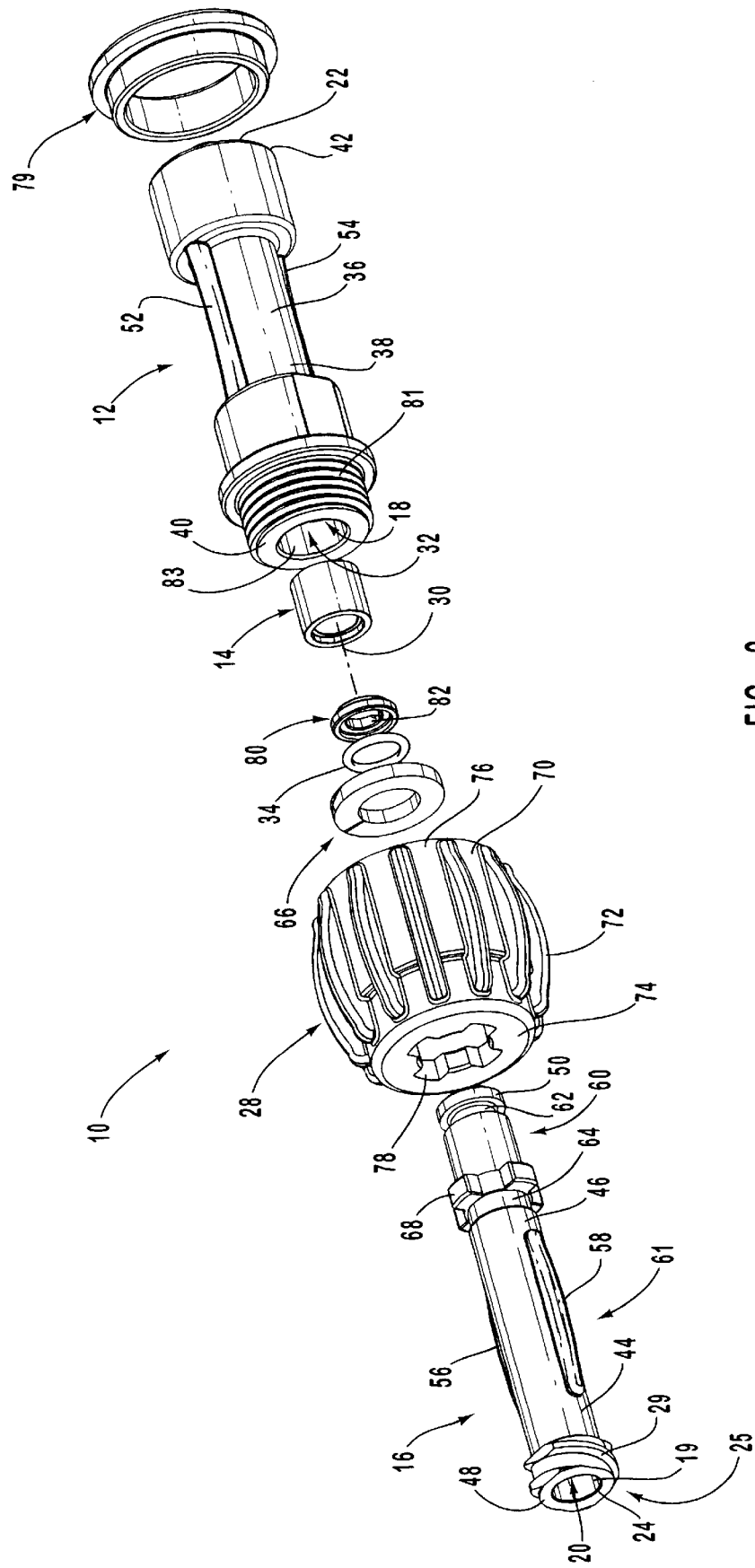
FIG. 2 is a perspective, exploded view of the valve apparatus of FIG. 1.

A hemostasis valve apparatus 10 of the present invention is shown in FIGS. 1 and 2. Valve 10 comprises: (i) a valve body 12; (ii) a first resiliently deformable seal 14 (FIG. 2) disposed within valve body 12; and (iii) a plunger 16 movably coupled to valve body 12.

Valve body 12 has an interior surface 17 defining a lumen 18 extending therethrough. Plunger 16 has an interior surface 19 defining a plunger lumen 20 extending therethrough which is in fluid communication with lumen 18 of valve body 12. Lumen 18 of valve body 12 has a distal valve opening 22 at a distal end 23 of valve 10 while plunger lumen 20 has a proximal valve opening 24 at a proximal end 25 of valve 10. Plunger 16 is movably coupled to valve body 12 such that a passageway 26 extends from distal valve opening 22 to proximal valve opening 24 through lumens 18, 20.

A hollow, rotatable cap 28 is movably coupled to valve body 12 for selectively moving plunger 16 back and forth with respect to valve body 12, thereby selectively opening and closing deformable seal 14.

A connector, e.g., proximal Luer connector 29, is coupled to plunger 16 for selectively coupling a fluid delivery means in fluid communication with passageway 26. This provides a valve 10 for selectively (i) injecting fluid through valve 10; and/or (ii) coupling an elongate instrument to valve 10. Luer connector 29 is an example of coupling means coupled to plunger 16 for coupling a fluid delivery means for delivering fluid in fluid communication with passageway 26. Connector 29 preferably extends integrally from the proximal end of plunger 16. Other examples of such coupling means include threads, grooves, detentes, spring loaded coupling mechanisms, pins, and a variety of other connectors configured to connect plunger 16 to a fluid delivery means. Connector 29 may be a male or female connector.

Similarly, distal Luer connector 31 is an example of means coupled to valve body 12 for coupling an object, such as an elongate tube (e.g., a catheter or introducer), or other object in fluid communication with passageway 26. Other examples of such coupling means include threads, grooves, detentes, spring loaded coupling mechanisms, pins, and a variety of other connectors.

In light of connector 29, which enables a fluid delivery means to be coupled to the proximal end of plunger 16, valve 10 can feature a substantially linear configuration, which is convenient for storage and use. Plunger 16 has a longitudinal axis and connector 29 is located along the longitudinal axis, thereby conserving space and providing for convenient use.

With reference now to FIG. 2, first seal 14 comprises a tubular seal. First seal 14 has an interior surface defining a longitudinal flow path 30 extending therethrough. Flow path 30 communicates with lumen 18 of valve body 12 when first seal 14 is in an open position. An elongated instrument, such as a catheter or guide wire, can be disposed through path 30 of seal 14. First seal 14 assumes a normally open position when not subjected to a compressive force, but responds to a compressive force to reduce the size of flow path 30. When a compressive force is exerted on seal 14, a portion of seal 14 moves radially inward to form a progressively tighter seal around a catheter or guide wire that is disposed in seal 14. The resiliently deformable seal 14 seats within a compression chamber 32 of valve body 12.

The amount of compressive force that is being exerted on seal 14 can be incrementally adjusted so as to selectively and progressively reduce the size of flow path 30. First seal 14 can thus couple to a delicate medical instrument such as a guidewire, occluding wire, coiled wire, or other wire, without crimping or otherwise damaging the instrument.

A variety of features of resilient seal 14 aid in this dynamic. First, seal 14 is resiliently deformable, thereby molding somewhat to the contour of a delicate instrument. Second, seal 14 is incrementally compressible such that flow path 30 extending through seal 14 can be selectively, adjustably narrowed a desired amount as cap 28 is rotated distally with respect to valve body 16.

In light of seal 14, valve 10 is useful as a steering device or handle, or a torquing device. A guide wire held within valve 10 can be manipulated to a desired position as the practitioner grips valve 10. Also by way of example, valve apparatus 10 may be used to firmly retain a coiled wire therein, such as a diagnostic wire. The diagnostic wire can be held within apparatus 10, then rotated or moved in and out as desired by a practitioner. The compressible seal holds the coiled wire firmly therein, but does not bend or crimp the wire.

Compressible seal 14 is one embodiment of structure capable of performing the function of a first sealing means disposed within body 12 for selectively sealing and unsealing lumen 18 of valve body 12 in response to a compressive force exerted on the first sealing means.

Compressible seal 14 preferably comprises a deformable, resilient material which allows compressible seal 14 to compress in response to a compressive force and either form a seal with itself or form a seal around an elongated instrument positioned through path 30. The material comprising compressible seal 14 should also be sufficiently resilient to enable compressible seal 14 to independently conform back to its original configuration when the compressive force is removed. The preferred material for tubular compressible seal 14 is silicon rubber. It is, however, contemplated that compressible seal 14 may be substantially composed of other kinds of conventional rubbers and elastomeric materials.

A second seal 34 seals passageway 26, which extends from distal valve opening 22 (FIG. 1) to proximal valve opening 24 through lumens 18, 20. Second seal 34 thus prevents fluid from flowing out of a location intermediate distal and proximal valve openings 22, 24. In the embodiment of FIG. 2, second seal 34 comprises an O-ring configured to be disposed about plunger 16.

Valve body 12 comprises an elongate tubular body 36 having a solid tubular body wall 38 extending from a proximal end 40 of tubular body 36 to a distal end 42 of tubular body 36. Valve body 12 comprises at least one and preferably a plurality of wings 52, 54 extending from tubular body 36 which act as a gripping surface when tubular body 36 is moved with respect to cap 28.

Plunger 16 also comprises a tubular body 44 having a solid tubular body wall 46 extending from a proximal end 48 of the tubular body to a distal end 50 of tubular body 46. Plunger 16 comprises at least one and preferably a plurality of wings 56, 58 extending from tubular body 36 which act as a gripping surface. Wings 56, 58 may be gripped, for example, when a practitioner desires to couple a fluid delivery means to plunger 16.

Tubular body 44 of plunger 16 has a distal neck portion 60 and a proximal gripping portion 61. Neck portion 60 has a first annular groove 62 therein, which is configured to receive O-ring 34 therein.

Neck portion 60 further has a second annular groove 64 therein which is configured to receive split ring 66 therein. Split ring 66 has a spiral cut therein. By way of example, split ring 66 can be mounted on neck 60 in accordance with principles disclosed the United States Patent entitled "Method for Positioning A Split Ring Over An Enlarged Flange," filed on Jul. 14, 1995, U.S. Pat. No. 5,651,170, and United States Patent entitled "Adaptor with Hemostasis Valve and Rotatable Connector," filed on Jul. 14, 1995, U.S. Pat. No. 5,693,025 each of which are incorporated herein by reference.

Extending from tubular body 44 of plunger 16 adjacent second annular groove 64 is a shoulder 68 which assists in the movement of plunger 16 and in the retaining of plunger 16 in a coupled relationship with valve body 12.

Each of the tubular bodies of plunger 16 and valve body 12 are substantially linear, thereby providing convenient storage and efficient use of space.

Rotatable cap 28 comprises a hollow main body 70 having a series of wings 72 thereon for assisting in the rotating of cap 28. Main body 70 includes an end wall 74 and an annular side wall 76 extending integrally and distally from end wall 74. An opening 78 within end wall 74 is configured to receive neck 60 therethrough during assembly. As shown, opening 78 is sized and configured to receive shoulder 68 of plunger 16 therethrough.

Rotatable cap 28 further comprises retaining ring 79 which is coupled to main body 70 of cap 28 during assembly of valve 10. Main body 70 of cap 28 is configured to selectively thread onto first engagement threads 81 of valve body 12 to thereby selectively advance plunger 16 within body 12.

FIG. 2 also illustrates a slip ring 80 which has an aperture 82 extending therethrough and is configured to fit in interlocking relationship between distal end 50 of plunger 16 and seal 14, such that plunger 16 exerts compressive force on seal 14 by exerting force on ring 80. In another embodiment, plunger 16 contacts seal 14 directly. Thus, plunger 16 can either compress seal 14 through direct or indirect contact with seal 14. The exterior surfaces of seal 14 and slip ring 80 are configured to mate within a portion of the interior surface 83 of compression chamber 32.

Figure 3:
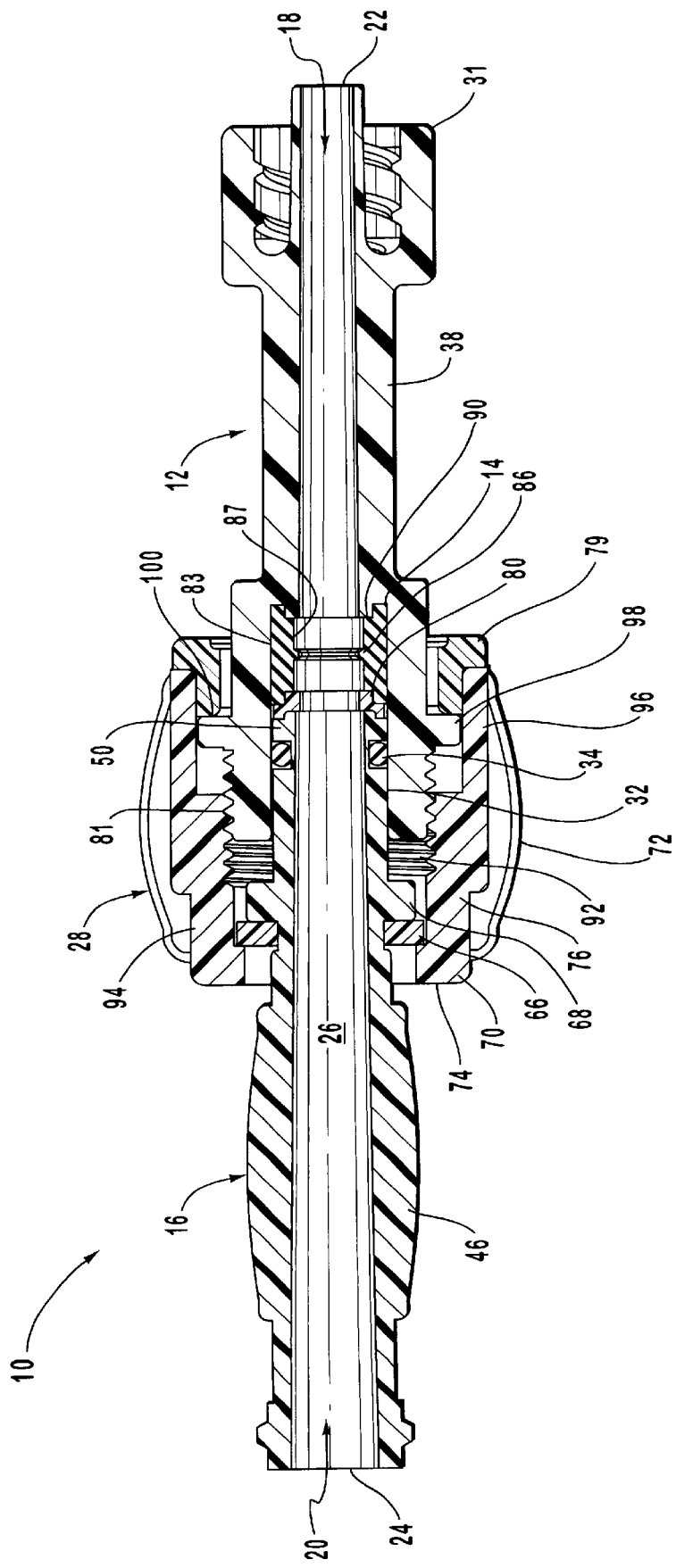
FIG. 3 is a view of the valve apparatus of FIG. 1 with the first seal in an open position.

With reference now to FIGS. 2 and 3, one technique for assembling valve 10 will now be described. First, seal 14 is placed within compression chamber 32, after which slip ring 80 is placed adjacent seal 14. Second seal 34 is disposed about neck 60 within first groove 62, after which neck 60 is passed through opening 78 in end wall 74 of cap 28 and split ring 66 is placed on second annular groove 64. Distal end 50 of neck 60 is then inserted into compression chamber 32 of valve body 12, after which main body 70 of cap 28 is threaded onto proximal end 40 of valve body 12. Retaining ring 79 is then coupled through the use of ultraviolet light activated adhesive, another adhesive, or another coupling means to main body 70.

FIG. 3 demonstrates a first position of plunger 16 in which distal end 50 of plunger 16 is disposed within compression chamber 32 of valve body 12 without compressing seal 14. Upon rotating cap 28, plunger 16 is moved distally within chamber 32, thereby compressing first seal 14.

In the embodiment shown, first seal 14 has recessed interior edges 90 such that first seal 14 is in a mating relationship with the distal end of compression chamber 32. It can be appreciated that the exterior surface of seal 14 may have other configurations as long as seal 14, chamber 32, and slip ring 80 are configured to cooperate.

A raised annular portion such as by way of example and not limitation, raised annular sealing rib 86, is integrally formed on the interior surface 87 of seal 14. Raised annular rib 86 may have various other configurations and perform the functions thereof equally effectively. By way of example and not limitation, a raised annular rib of the present invention may be shaped as semi-spherical, half an ellipse, semi-circular, rectangular, half an octagon, or various other shapes.

As compressible seal 14 compresses radially inward, seal 14 simultaneously compresses radially outwardly against the interior surface 83 of chamber 32 so as to form a seal therebetween. Plunger 16 can continue to be advanced until raised annular rib 86 is pressed together against itself to completely close and seal passageway 30 through compressible seal 14.

Rib 86 is configured to allow an elongated instrument accessing passageway 26 to be repositioned or removed while still maintaining a seal capable of preventing substantially all loss of body fluids beyond seal 14 without releasing substantially all of the compressive force acting on seal 14. Other embodiments including alternative structures capable of performing the function of such a first sealing means may be equally effective in carrying out the intended function thereof. In yet another embodiment, seal 14 is employed without a rib 86, but merely includes a smooth interior surface.

Slip ring 80 is in an interlocking relationship disposed between first seal 14 and plunger 16. Slip ring 80 provides a smooth surface for contact with plunger 16 which prevents the twisting of first seal 14 during rotation of plunger 16 within chamber 32, such as when a fluid delivery means is coupled to plunger 16 and plunger 16 is rotated.

Extending from annular side wall 76 of cap 28 is a set of second engagement threads 92 configured for rotational, threaded engagement with first engagement threads 81 on proximal end 40 of valve body 12. Sidewall 76 has a thinner, proximal portion 94 and a wider, distal portion 96. Threads 92 extend from thinner proximal portion 94 for engagement with threads 81 of body 12. Wider distal portion 96 fits over a shoulder 98 extending from a proximal portion of body 12. Shoulder 98 of body 12 acts as a stop when contacted by the proximal edge 100 of retaining ring 79 as cap 28 is moved proximally during the opening of valve 14.

In the embodiment of FIG. 3, cap 28 can be rotated without rotating plunger 16. End wall 74 of cap 28 engages slit ring 66 in an abutting relationship, rather than being fused to plunger 16. Slit ring 66 is retained within second groove 64 and engages shoulder 68 of plunger 16 in an abutting relationship such that cap 28 moves plunger 16 distally as cap 28 is threaded distally along body 12. In another embodiment (not shown), plunger 16 is affixed to cap 28 and rotates with cap 28, such as by being fused to cap 28.

However, since plunger 16 can be rotated independently from cap 28, a fluid delivery means can be selectively coupled to plunger 16 by rotating plunger 16 with respect to the fluid delivery means without necessarily rotating body 12 or cap 28.

Rotatable cap 28 is one example of structure capable of performing the function of a means for movably coupling plunger 16 to a proximal end of body 12. Cap 28 movably couples plunger 16 to valve body 12. As mentioned above, when cap 28 moves in a distal direction, end wall 74 of cap 28 engages split ring 66, moving plunger 16 distally and thereby exerting force on seal 14. When cap 28 moves in a proximal direction, compressed valve 14 forces plunger 16 in a proximal direction and decompresses into the open position.

As another embodiment of structure capable of performing the function of a means for movably coupling the plunger to a proximal end of a valve body, a plunger (not shown) has threads extending therefrom which selectively thread with threads extending from an interior surface of a valve body.

A plunger and the means for movably coupling the plunger to the valve body serve collectively as an example of compressing means movably coupled to body 12 for selectively increasing and decreasing compressive force on compression seal 14. The compression force is increased when cap 28 is rotated in one direction relative to body 12 and is gradually decreased when cap 28 is rotated in the opposite direction relative to body 12. Various embodiments of structure capable of performing the function of such a compressing means are equally effective in carrying out the intended function thereof, including a cap integrally extending from a plunger which movably couples the plunger to body 12, the cap configured such that movement of the cap along the body 12 moves the plunger along the body 12.

Seal 34 is disposed about distal end 50 of plunger 16, which is inserted within valve body 12. Resilient second seal 34 is shown as abutting both plunger 16 and the interior surface 83 of compression chamber 32 of valve body 12. Second seal 14 is preferably compressed between distal end 50 of plunger 16 and interior surface 83 of compression chamber 32. Seal 34 abuts and slides along the interior surface 83 of compression chamber 32 when plunger 16 is moved back and forth within valve body 12, thereby providing a seal, preventing fluid from passing from passageway 26 to the threads of valve 10.

Figure 4:
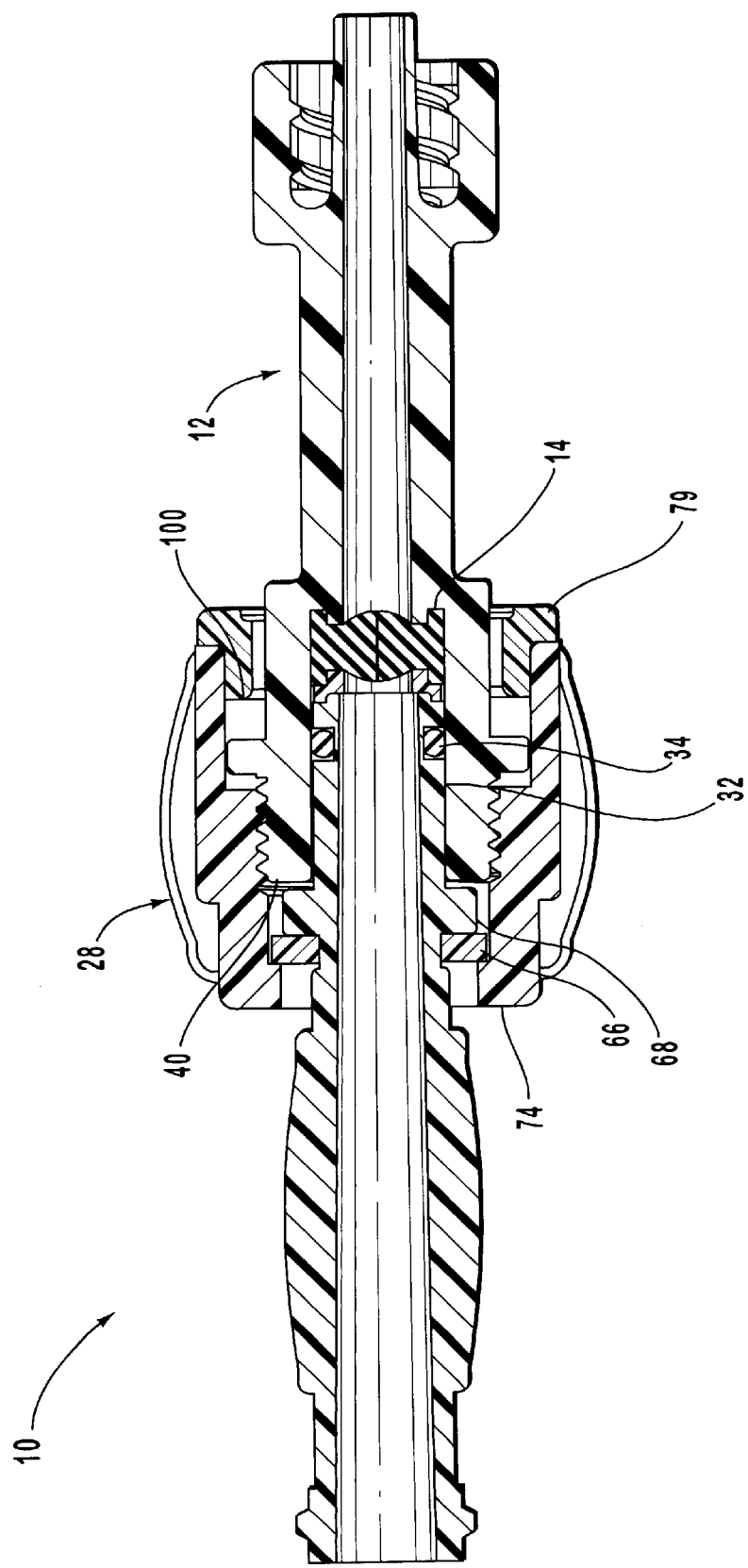
FIG. 4 is a view of the valve apparatus of FIG. 1 with the first seal in a closed position.

With reference now to FIG. 4, plunger 16 is shown in a second, distal position, and seal 14 is shown in a closed position. In this position, seal 14 is configured to substantially block and control the loss of fluids from passageway 26. Shoulder 68 of plunger 16 can be configured to act as a stop against proximal end 40 of valve body 12 as plunger 16 is advanced to the second, distal position.

By moving back and forth between the first, proximal position (FIG. 3) and the second, distal position (FIG. 4) within valve body 12, plunger 16 selectively opens and closes first seal 14, respectively. Cap 28 is rotatable such that compressive force can be increased when cap 28 is rotated in one direction relative to valve body 12 and such that compressive force can be decreased when cap 28 is rotated in an opposite direction relative to the valve body 12.

In the compressed position of FIG. 4, seal 14 can conveniently grip delicate medical instruments therein. A practitioner can then twist or rotate the elongate medical instrument by twisting valve 10. Valve 10 is thus an example of a torquing device.

Figure 5:
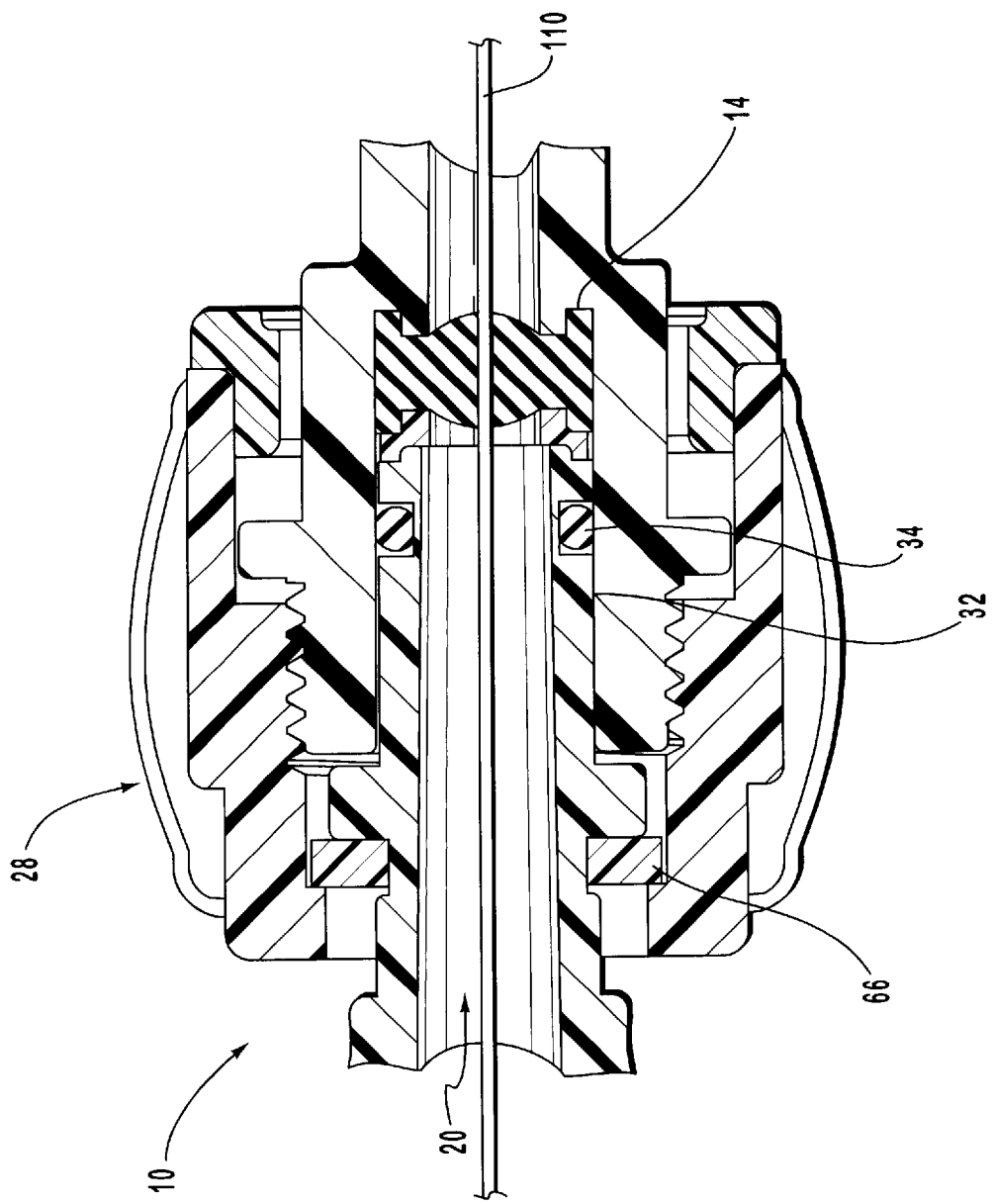
FIG. 5 is a view of the valve apparatus of FIG. 1 with the first seal closed about a wire extending through the valve apparatus.
Figure 6:
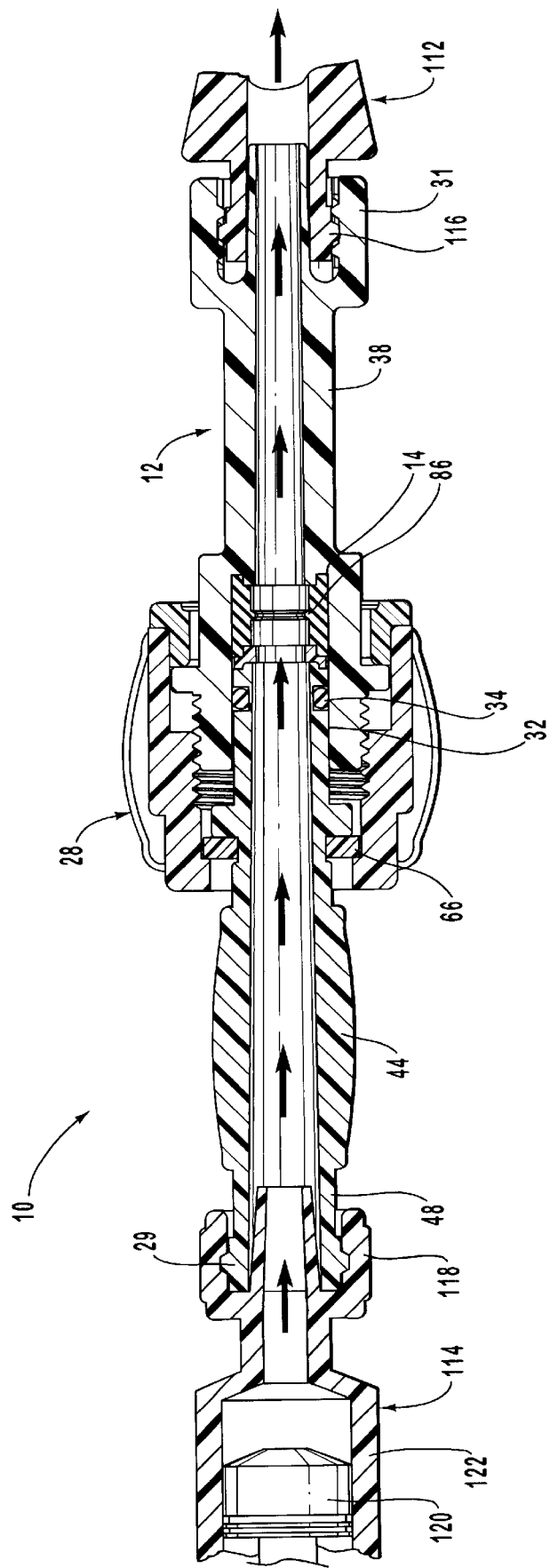
FIG. 6 is a view of the valve apparatus of FIG. 1 with the valve apparatus selectively coupled at a proximal end thereof to a fluid delivery means and with a distal end thereof selectively coupled to a catheter. The first seal is opened, the arrows demonstrating the direction of fluid flow from the fluid delivery means through the valve and the catheter.

With reference now to FIGS. 5 and 6, according to one technique, a guide wire 110 is disposed through valve apparatus 10. Seal 14 firmly retains guide wire 110 in a fixed position within valve apparatus 10 without damaging guide wire 110. Valve apparatus 10 can then be employed to retain wire 110 in a fixed position or to guide or steer guide wire 110 or another elongate member into a desired location within the cardiovascular system of a patient, for example.

With reference now to FIG. 6, connector 31 of valve apparatus 10 can be selectively coupled to a hub 116 of a catheter 112 or introducer, thereby coupling catheter 112 in fluid communication with valve 10. After guiding a guidewire and/or a catheter 112 to a desired location within the body of a patient, the guidewire can then be removed.

A mating Luer connector 118 of syringe 114 (or a fluid pump, motorized power injection device, or other fluid delivery means) can then be selectively coupled to connector of plunger 16, after which syringe plunger 120 is compressed within syringe barrel 122 to thereby inject fluid through valve 16, catheter 112 and into the patient.

Plunger body 36 and valve body 44 withstand significant fluid pressures during this process and second seal 34 assists by sealing passageway 26 defined by respective valve bodies 36, 44. In one embodiment, valve apparatus 10 is capable of withstanding pressures as high as 1050 psi, or more, in the open position of FIG. 6.

Valve body 12 a structure capable of performing the function of a body means for providing a lumen 18 therethrough. It can be appreciated that various other embodiments of a body means may be equally effective in carrying out the intended function thereof.

Cap 28, body 12, and plunger 16 preferably comprises a clear, transparent polycarbonate plastic. Such a plastic material allows for relatively easy molding, moderate flexibility, and the ability to see the internal components and operation of the adapters. Of course, alternative types of conventional plastics can also be used depending on one's taste and the intended use of a particular adaptor. Seal 34 is preferably comprised of silicon rubber. It is, however, contemplated that seal 34 may be substantially composed of other kinds of conventional rubbers and elastomeric materials.

To facilitate slippage between plunger 16 and slip ring 80, slip ring 80 may be made of a relatively rigid material having a relatively low coefficient of friction, such as Delrin or polytetrafluorethylene, or more commonly known as Teflon®. Split ring 66 may also be comprised of Delrin or polytetrafluorethylene, commonly known as Teflon®, to assist in rotational slipping between plunger 16 and slip ring 80 and to provide a smoother interaction between the components within valve assembly 10, a small quantity of oil or other lubrication, such as medical grade silicone oil, can be used to lubricate the interactive components of valve assembly 10.

For example, the interior surface 87 of seal 14 can be coated with an oil to prevent interior surface 87 and raised annular rib 86 from sticking together as end cap 28 is retracted proximally to open path 30 through compressible seal 14.

Examples of fluid delivery means for delivering fluid which can be used in conjunction with valve 10 include syringes, pumps, reservoirs, squeeze bottles, fluid bags, pressurized tanks, motorized power injection devices, and other containers or devices which are configured or positioned so as to deliver fluid to valve 10.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for providing, in combination, a hemostasis valve, a steering device for an intravascular instrument such as guidewire, and a fluid coupling device for attachment to a fluid delivery system, comprising:

means for providing a single, straight passageway through which either an intravascular instrument or fluids are introduced, as selected;

means, disposed within said passageway, for selectively sealing and unsealing said passageway in response to a compressive force exerted on said means for selectively sealing and unsealing said passageway, the means for selectively sealing and unsealing said passageway assuming a normally open position when not subjected to said compressive force, and responding to said compressive force so as to selectively and progressively reduce the size of said passageway; and a single means for both (i) selectively increasing and decreasing said compressive force, and (ii) rotatable attachment of said passageway to a fluid delivery system.

2. An apparatus as recited in claim 1, wherein said sealing means comprises a resiliently deformable, compressible annular seal.

3. An apparatus as recited in claim 1, wherein said means for providing a single, straight passageway comprises a means for forming a body of the apparatus, and wherein said body means comprises a substantially linear, tubular body.

4. An apparatus as recited in claim 3, wherein the body means comprises a tubular body having a solid tubular body wall extending from a proximal end of the tubular body to the distal end of the tubular body.

5. An apparatus as recited in claim 3, wherein said body means is comprised of a means for coupling the apparatus at opposite ends thereof, and wherein said coupling means comprises a Luer connector at each said end.

6. An apparatus as recited in claim 3, further comprising a means for exerting said compressive force, and wherein said compressing means comprises (i) a plunger; and (ii) means for movably coupling the plunger to a proximal end of the body means.

7. An apparatus as recited in claim 6, wherein the means for movably coupling the plunger to a proximal end of the body means comprises a cap movably coupled to the body means, the cap configured such that movement of the cap along the body means moves the plunger along the body means.

8. An apparatus as recited in claim 7, wherein the plunger is rotatable independently from the cap.

9. An apparatus as recited in claim 1, wherein the apparatus has a substantially linear configuration.

10. An apparatus for providing, in combination, a hemostasis valve, a steering device for an intravascular instrument such as a guidewire, and a fluid coupling device for attachment to a fluid delivery system, comprising:

an elongated hollow valve body which provides a first lumen and which can be grasped and rotated when steering an intravascular instrument, and which comprises a coupling at one end thereof, an elongated tubular body which provides a second lumen and which can be grasped and rotated independently of the valve body, the first and second lumens being joined together to form a single, continuous, straight passageway;

a compressible seal disposed between said first and second lumens and operable in response to a compressive force exerted on the compressible seal to selectively and progressively reduce the size of the passageway so as to either close the passageway, or so as to securely clamp an intravascular instrument within said passageway in a completely fluid tight and non-slip manner to permit steering as well as preventing blood loss;

a rotatable cap for joining the tubular body to the valve body, said rotatable cap being operable to exert said compressive force against the compressible seal as it is rotated one way to tighten the tubular body against the compressible seal, and being operable to remove said compressive force against the compressible seal as it is rotated in an opposite way; and one end of said tubular body being rotatably disposed and sealed within said cap so that the tubular body can be selectively rotated within said cap independently of the cap's rotation, and an opposite end of the tubular body comprising a coupling.

11. An apparatus as recited in claim 10, wherein the valve body comprises a substantially linear, tubular body.

12. An apparatus as recited in claim 10, further comprising a second seal configured to seal the passageway.

13. A valve apparatus as recited in claim 12, wherein the second seal comprises an O-ring.

14. An apparatus as recited in claim 13, wherein the elongated tubular body which provides said second lumen has a groove in the distal end thereof, the O-ring disposed within the groove in abutting, sliding engagement with an interior surface of the valve body.

* * * * *

UNITED STATES PATENT AND TRADEMARK OFFICE
CERTIFICATE OF CORRECTION

PATENT NO. : 6,402,723 B1
DATED : June 11, 2002
INVENTOR(S) : Fred P. Lampropoulos and Brian W. Stevens It is certified that error appears in the above-identified patent and that said Letters Patent is hereby corrected as shown below:

<u>Column 5,</u>
Line 49, after "seal 14" please delete "seats" and insert -- sits --

<u>Column 6,</u>
Line 54, after "principles disclosed" please insert -- in --

<u>Column 7,</u>
Line 16, after "to fit in" please insert -- an --

<u>Column 9,</u>
Line 53, after "coupled to connector" please insert -- 29 --
Line 63, after "Valve body 12" please insert -- is --

Signed and Sealed this

Sixth Day of April, 2004

JON W. DUDAS
*Acting Director of the United States Patent and Trademark Office*